US008293465B2

(12) United States Patent
Chang et al.

(10) Patent No.: US 8,293,465 B2

(45) Date of Patent: Oct. 23, 2012

(54) METHOD FOR THE DETECTION OF HUMAN IMMUNODEFICIENCY VIRUS ENVELOPE (HIV) GLYCOPROTEIN UTILIZING CARBOHYDRATE BINDING MODULE (CBM) 20 OR 21

(75) Inventors: Margaret Dah-Tsyr Chang, Hsinchu (TW); Yuan-Chuan Lee, Hsinchu (TW); Rong-Yuan Huang, Hsinchu (TW); Shu-Chuan Lin, Hsinchu (TW); Wei-I Chou, Hsinchu (TW); Shi-Hwei Liu, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 23 days.

(21) Appl. No.: 12/755,242

(22) Filed: Apr. 6, 2010

(65) Prior Publication Data

US 2010/0291601 A1 Nov. 18, 2010

Related U.S. Application Data

(62) Division of application No. 12/464,788, filed on May 12, 2009.

(51) Int. Cl.
*C12Q 1/70* (2006.01)
*C12Q 1/40* (2006.01)
*A61K 39/21* (2006.01)
*A61K 36/00* (2006.01)

(52) U.S. Cl. ............ 435/5; 435/22; 424/208.1; 530/370

(58) Field of Classification Search ........................ None
See application file for complete search history.

(56) References Cited

OTHER PUBLICATIONS

Boraston, A. B., et al., 2004, Carbohydrate-binding modules: fine-tuning polysaccharide recognition, Biochem. J. 382:769-781.*
Lammerts, A., et al., 2007, The structural basis of alpha-glucan recognition by a family 41 carbohydrate-binding module from *Thermotoga maritima*, J. Mol. Biol. 365:555-560.*
Trkola, A., et al., 1996, Human monoclonal antibody 2G12 defines a distinctive neutralization epitope on the gp120 glycoprotein of human immunodeficiency virus type 1, J. Virol. 70(2):1100-1108.*
Richardson, Jr., T. M., et al., Feb. 1996, Humoral response to oligomeric human immunodeficiency virus type 1 envelope protein, J. Virol. 70(2):753-762.*
Gurtler, L., et al., 1998, Reduction of the diagnostic window with a new combined p24 antigen and human immunodeficiency virus antibody screening assay, J. Virol. Methods 75:27-38.*

* cited by examiner

*Primary Examiner* — Jeffrey S. Parkin
(74) *Attorney, Agent, or Firm* — WPAT, P.C.; Anthony King

(57) ABSTRACT

The present invention relates to an antibody mimetic of carbohydrate binding module (CBM) which specifically binds to an epitope on HIV glycoprotein. The present invention also relates to a method of detecting HIV glycoprotein.

9 Claims, 9 Drawing Sheets

| Chart # | Masterlist Name | RFU | STDEV | SEM | %CV |
|---|---|---|---|---|---|
| 187 | $Man_{\alpha 1-2}Man_{\alpha 1-2}Man_{\alpha 1-3}Man_{\alpha}$-Sp9 | 6129 | 492 | 246 | 8 |

Chemical Formula: $C_{24}H_{42}O_{21}$
Molecular Weight: 666.5777

2G12 (PDB ID: 1ZLS) *Ro*SBD (PDB ID: 2V8M)

| Superimpose with CBM21 (2V8M) | RMSD value |
|---|---|
| 2G12 (1ZLS) | 2.43 Å |

Figure 3

Structure-based sequence alignment

```
RoCBM21 (SEQ ID NO. 2)    1 -AS-IPSSAS-VQL-DSYNYD-G-STFSGKIYVKN-I-AY-SKKVTVVYADG-SDNWNNNGNIIAASFSG    60

1ZLS:H (SEQ ID NO. 1)     1 EVQLVESGGGLVKAGGSLILSCGVSNFRISAHTMNWVRRVPGGGLEWVASISTSSTYRDYADAVKGRFTV    70


RoCBM21 (SEQ ID NO. 2)      PISG-SNYEYWTFSA-SVKGIKEFYIKYEVSGK------TYYDN-NNSANYQVS---T    106

1ZLS:H (SEQ ID NO. 1)       SRDDLEDFVYLQMHKMRVEDTAIYYCARKGSDRLSDNDPFDAWGPGTVVTVSPAS    125
```

Identity: 8.9%

Figure 8 A

2G12 (SEQ ID NO. 3) NCTRPNNNTRKRIRIQRGPGRAFVTIGKIGNMRQAHCNISRAKWNNTLKQIASKLREQFGNNKTIIFKQSSGGDPEIVTH

HXB2 (SEQ ID NO. 4) NCTRPNNNTRKRIRIQRGPGRAFVTIGKIGNMRQAHCNISRAKWNNTLKQIASKLREQFGNNKTIIFKQSSGGDPEIVTH

LW892 (SEQ ID NO. 5) NCTRPNNNTRKRIRIQRGPGRAFVTIGKIGNMRQAHCNISRAKWNNTLKQIASKLREQFGNNKTIIFKQSSGGDPEIVTH wt1 (SEQ ID NO. 6) NCTRPNNNTRKKIRIQRGPGRAFVTIGKIGNMRQAHCNISRAKWNATLKQIASKLREQFGNNKTIIFKQSSGGDPEIVTH

MCK1 (SEQ ID NO. 7) NCTRPNNNTRKRIRIQRGPGRAFVTIGKIGNMRQAHCNISRAKWNATLKQIASKLREQFGNNKTIIFKQSSGGDPEIVTH

CH69-2 (SEQ ID NO. 8) NCTRPNNNTRKKIRIQRGPGRAFVTIGKIGNMRQAHCNISRAKWNATLKQIASKLREQFGNNKTIIFKQSSGGDPEIVTH

XB3 (SEQ ID NO. 9) NCTRPNNNTRKKIRIQRGPGRAFVTIGKIGNMRQAHCNISRAKWNATLKQIASKLREQFGNNKTIIFKQSSGGDPEIVTH wt2 (SEQ ID NO. 10) NCTRPNNNTRKKIRIQRGPGRAFVTIGKIGNMRQAHCNISRAKWNATLKQIDSKLREQFGNNKTIIFKQSSGGDPEIVTH

LW12.3 (SEQ ID NO.11) NCTRPNNNTRKRIRIQRGPGRTFVTIGKIGNMRQAHCNISRAKWNATLKQIASKLREQFGNNKTIIFKQSSGGDPEIVTH

BH10 (SEQ ID NO.12) NCTRPNNNTRKSIRIQRGPGRAFVTIGKIGNMRQAHCNISRAKWNNTLKQIDSKLREQFGNNKTIIFKQSSGGDPEIVTH

PV22 (SEQ ID NO.13) NCTRPNNNTRKSIRIQRGPGRAFVTIGKIGNMRQAHCNISRAKWNNTLKQIDSKLREQFGNNKTIIFKQSSGGDPEIVTH

BRU (SEQ ID NO.14) NCTRPNNNTRKSIRIQRGPGRAFVTIGKIGNMRQAHCNISRAKWNATLKQIASKLREQFGNNKTIIFKQSSGGDPEIVTH

CH69-7 (SEQ ID NO.15) NCTRPNNNTRKKIRIQRGPGRAFVTLGKIGNMRQAHCNISRAKWNATLKQIASKLREQFGSNKTIIFKQSSGGDPEIVTH

1H6 (SEQ ID NO.16) NCTRPNNNTRKKIRIQRGPGRTFVTIGKIGNMRQAHCNISRAKWNATLKQIDSKLREQFGNNKTIIFKQSSGGDPEIVTH

1F8 (SEQ ID NO.17) NCTRPNNNTRKKIRIQRGPGRALVTIGKIGNMRQAHCNISRAKWNATLKQIDSKLREQFGNNKTIIFKQSSGGDPEIVTH

MfA (SEQ ID NO.18) NCTRPNNNTRKSIRIQRGPGRAFVTIGKIGNMRQAHCNISRAKWMNTLKQIASKLREQFGNNKTVIFKQSSGGDPEIVTH

CH69-6 (SEQ ID NO.19) NCIRPNNNTRKKIRIQRGPGRALVTIGKIGNMRQAHCNISRAKWNATLKQIASKLREQFGNNKTIIFKQSSGGDPEIVTH

CH69 5 (SEQ ID NO.20) NCIRPNNNTRKKIRIQRGPGRALVTIGKIGNMRQAHCNISRAKWNATLKQIASKLREQFGNNKTIIFKQSSGGDPEIVTH

1B6 (SEQ ID NO.21) NCTRPNNNTRKKIRIQRGPGRTFDTIGKIGNMRQAHCNISRAKWNATLKQIDSKLREQFGNNKTIIFKQSSGGDPEIVTH

CH69-1 (SEQ ID NO.22) NCARPNNNTRKKIRIRRGPGRAFVTIGKIGNMRQAHCNISRAKWNATLKQIASKLREQFGNNKTIIFKQSSGGDPEIVAH

TH4 7 5 (SEQ ID NO.23) NCTRPNNNTRKSIRIQRGPGRAFVTIGKIGNMRQAHCNISRAKWNNTLKQIASKLREQFGNNKTIIFKQSSGGDPEIVTH

Gp160 (SEQ ID NO.24) NCTRPYNNKRKSIRIQRGPGRAFVTIGKIGNMRQAHCNISRAKWNATLKQIASKLREQFGNNKTIIFKQSSGGDPEIVTH

Figure 8 B

2G12 (SEQ ID NO. 3) SFNCGGEFFYCNSTQLFNSTWFNSTWSTEGSNNTEGSDTITLPCRIKQIINMWQKVGKAMYAPPISGQIRCSSN

HXB2 (SEQ ID NO. 4) SFNCGGEFFYCNSTQLFNSTWFNSTWSTEGSNNTEGSDTITLPCRIKQIINMWQKVGKAMYAPPISGQIRCSSN

LW892 (SEQ ID NO. 5) SFNCGGEFFYCNSTQLFNSTWFNSTWSTEGSNNTEGSDTITLPCRIKQIINMWQEVGKAMYAPPISGQIRCSSN wt1 (SEQ ID NO. 6) SFNCGGEFFYCNSTQLFNSTWFNSTWSTEGSNNTEGSDTITLPCRIKQIINMWQEVGKAMYAPPISGQIRCSSN

MCK1 (SEQ ID NO. 7) SFNCGGEFFYCNSTQLFNSTWFNSTWSTEGSNNTEGSDTITLPCRIKQFINMWQEVGKAMYAPPISGQIRCSSN

CH69-2 (SEQ ID NO. 8) SFNCGGEFFYCNSTQLFNSTWFNSTWSTEGSNNTEGSDTITLPCRIKQIINMWQEVGKAMYAPPISGQIRCSSN

XB3 (SEQ ID NO. 9) SFNCGGEFFYCNSTQLFNSTWFNSTWSTEGSNNTEGSDTITLPCRIKQFINMWQEVGKAMYAPPISGQIRCSSN wt2 (SEQ ID NO.10) SFNCGGEFFYCNSTQLFNSTWFNSTWSTEGSNNTEGSDTITLPCRIKQIINMWQEVGKAMYAPPISGQIRCSSN

LW12.3 (SEQ ID NO.11) SFNCGGEFFYCNSTQLFNSTWFNSTWSTEGSNNTEGSDTITLPCRIKQIINMWQEVGKAMYAPPISGQIRCSSN

BH10 (SEQ ID NO.12) SFNCGGEFFYCNSTQLFNSTWFNSTWSTKGSNNTEGSDTITLPCRIKQIINMWQEVGKAMYAPPISGQIRCSSN

PV22 (SEQ ID NO.13) SFNCGGEFFYCNSTQLFNSTWFNSTWSTEGSNNTEGSDTITLPCRIKQFINMWQEVGKAMYAPPISGQIRCSSN

BRU (SEQ ID NO.14) SFNCGGEFFYCNSTQLFNSTWFNSTWSTEGSNNTEGSDTITLPCRIKQFINMWQEVGKAMYAPPISGQIRCSSN

CH69-7 (SEQ ID NO.15) SFNCGGEFFYCNSTQLFNSTWFNSTWSTEGSNNTEGSDTITLPCRIKQIINMWQEVGKAMYAPPISGQIRCSSN

1H6 (SEQ ID NO.16) SFNCGGEFFYCNSTQLFNSTWFNSTWSTEGSNNTEGSDTITLPCRIKQIINMWQEVGKAMYAPPISGQIRCSSN

1F8 (SEQ ID NO.17) SFNCGGEFFYCNSTQLFNSTWFNSTWSTEGSNNTEGSDTITLPCRIKQIINMWQEVGKAMYAPPISGQIRCSSN mfA (SEQ ID NO.18) SFNCGGEFFYCNSTQLFNSTWFNSTWSTEGSNNTEGSDTITLPCRIKQFINMWQEVGKAMYAPPISGQIRCSSN

CH69-6 (SEQ ID NO.19) SFNCGGEFFYCNSTQLFNSTWFNSTWSTEGSNNAEGSDTITLPCRIKQIINMWQEVGKAMYAPPISGQIRCSSN

CH69-5 (SEQ ID NO.20) SFNCGGEFFYCNSTQLFNSTWFNSTWSTEGSNNAEGSDTITLPCRIKQIINMWQEVGKAMYAPPISGQIRCSSN

1B6 (SEQ ID NO.21) SFNCGGEFFYCNSTQLFNSTWFNSTWSTEGSNNTEGSDTITLPCRIKQIINMWQEVGKAMYAPPISGQIRCSSN

CH69-1 (SEQ ID NO.22) SFNCGGEFFYCNSTQLFNSTWFNSTWSTEGSNNTEGSDTITLPCRIKQIINMWQEVGKAMYAPPISGQIRCSSN

TH4-7-5 (SEQ ID NO.23)SFNCGGEFFYCNSTQLFNSTWSNSTLSTEGSNNTEGSDTITLPCRIKQIINMWQEVGKAMYAPPISGQIRCSSN

Gp160 (SEQ ID NO.24) SFNCGGEFFYCNSTQLFNSTWFNSTWSTEESNSTEGSDTITLPCRIKQFINMWQKVGKAMYAPPISGQIRCS

SEQUENCE LISTING

```
<160> NUMBER OF SEQ ID NOS: 24

<210> SEQ ID NO 1
<211> LENGTH: 123
<212> TYPE: PRT
<213> ORGANISM: Artificial
<220> FEATURE:
<223> OTHER INFORMATION: VH domain of 2G12 antibody
<220> FEATURE:
<221> NAME/KEY: DOMAIN
<222> LOCATION: (1)..(123)

<400> SEQUENCE: 1

Glu Val Gln Leu Val Glu Ser Gly Gly Gly Leu Val Lys Ala Gly Gly
1               5                   10                  15

Ser Leu Ile Leu Ser Cys Gly Val Ser Asn Phe Arg Ile Ser Ala His
            20                  25                  30
```

```
Thr Met Asn Trp Val Arg Arg Val Pro Gly Gly Gly Leu Glu Trp Val
        35                  40                  45

Ala Ser Ile Ser Thr Ser Ser Thr Tyr Arg Asp Tyr Ala Asp Ala Val
    50                  55                  60

Lys Gly Arg Phe Thr Val Ser Arg Asp Asp Leu Glu Asp Phe Val Tyr
65                  70                  75                  80

Leu Gln Met His Lys Met Arg Val Glu Asp Thr Ala Ile Tyr Tyr Cys
                85                  90                  95

Ala Arg Lys Gly Ser Asp Arg Leu Ser Asp Asn Asp Pro Phe Asp Ala
            100                 105                 110

Trp Gly Pro Gly Thr Val Val Thr Val Ser Pro
        115                 120


<210> SEQ ID NO 2
<211> LENGTH: 106
<212> TYPE: PRT
<213> ORGANISM: Rhizopus oryzae
<220> FEATURE:
<221> NAME/KEY: DOMAIN
<222> LOCATION: (1)..(106)

<400> SEQUENCE: 2

Ala Ser Ile Pro Ser Ser Ala Ser Val Gln Leu Asp Ser Tyr Asn Tyr
1               5                   10                  15

Asp Gly Ser Thr Phe Ser Gly Lys Ile Tyr Val Lys Asn Ile Ala Tyr
            20                  25                  30

Ser Lys Lys Val Thr Val Val Tyr Ala Asp Gly Ser Asp Asn Trp Asn
        35                  40                  45

Asn Asn Gly Asn Ile Ile Ala Ala Ser Phe Ser Gly Pro Ile Ser Gly
    50                  55                  60

Ser Asn Tyr Glu Tyr Trp Thr Phe Ser Ala Ser Val Lys Gly Ile Lys
65                  70                  75                  80

Glu Phe Tyr Ile Lys Tyr Glu Val Ser Gly Lys Thr Tyr Tyr Asp Asn
                85                  90                  95

Asn Asn Ser Ala Asn Tyr Gln Val Ser Thr
            100                 105


<210> SEQ ID NO 3
<211> LENGTH: 154
<212> TYPE: PRT
<213> ORGANISM: Artificial
<220> FEATURE:
<223> OTHER INFORMATION: antibody
<220> FEATURE:
<221> NAME/KEY: DOMAIN
<222> LOCATION: (1)..(154)

<400> SEQUENCE: 3

Asn Cys Thr Arg Pro Asn Asn Asn Thr Arg Lys Arg Ile Arg Ile Gln
1               5                   10                  15

Arg Gly Pro Gly Arg Ala Phe Val Thr Ile Gly Lys Ile Gly Asn Met
            20                  25                  30

Arg Gln Ala His Cys Asn Ile Ser Arg Ala Lys Trp Asn Asn Thr Leu
        35                  40                  45

Lys Gln Ile Ala Ser Lys Leu Arg Glu Gln Phe Gly Asn Asn Lys Thr
    50                  55                  60

Ile Ile Phe Lys Gln Ser Ser Gly Gly Asp Pro Glu Ile Val Thr His
65                  70                  75                  80

Ser Phe Asn Cys Gly Gly Glu Phe Phe Tyr Cys Asn Ser Thr Gln Leu
```

-continued

```
                85                  90                  95

Phe Asn Ser Thr Trp Phe Asn Ser Thr Trp Ser Thr Glu Gly Ser Asn
            100                 105                 110

Asn Thr Glu Gly Ser Asp Thr Ile Thr Leu Pro Cys Arg Ile Lys Gln
        115                 120                 125

Ile Ile Asn Met Trp Gln Lys Val Gly Lys Ala Met Tyr Ala Pro Pro
    130                 135                 140

Ile Ser Gly Gln Ile Arg Cys Ser Ser Asn
145                 150


<210> SEQ ID NO 4
<211> LENGTH: 154
<212> TYPE: PRT
<213> ORGANISM: Human immunodeficiency virus type 1
<220> FEATURE:
<221> NAME/KEY: MISC_FEATURE
<222> LOCATION: (1)..(154)
<223> OTHER INFORMATION: HXB2

<400> SEQUENCE: 4

Asn Cys Thr Arg Pro Asn Asn Asn Thr Arg Lys Arg Ile Arg Ile Gln
1               5                   10                  15

Arg Gly Pro Gly Arg Ala Phe Val Thr Ile Gly Lys Ile Gly Asn Met
            20                  25                  30

Arg Gln Ala His Cys Asn Ile Ser Arg Ala Lys Trp Asn Asn Thr Leu
        35                  40                  45

Lys Gln Ile Ala Ser Lys Leu Arg Glu Gln Phe Gly Asn Asn Lys Thr
    50                  55                  60

Ile Ile Phe Lys Gln Ser Ser Gly Gly Asp Pro Glu Ile Val Thr His
65                  70                  75                  80

Ser Phe Asn Cys Gly Gly Glu Phe Phe Tyr Cys Asn Ser Thr Gln Leu
                85                  90                  95

Phe Asn Ser Thr Trp Phe Asn Ser Thr Trp Ser Thr Glu Gly Ser Asn
            100                 105                 110

Asn Thr Glu Gly Ser Asp Thr Ile Thr Leu Pro Cys Arg Ile Lys Gln
        115                 120                 125

Ile Ile Asn Met Trp Gln Lys Val Gly Lys Ala Met Tyr Ala Pro Pro
    130                 135                 140

Ile Ser Gly Gln Ile Arg Cys Ser Ser Asn
145                 150


<210> SEQ ID NO 5
<211> LENGTH: 154
<212> TYPE: PRT
<213> ORGANISM: Human immunodeficiency virus type 1
<220> FEATURE:
<221> NAME/KEY: MISC_FEATURE
<222> LOCATION: (1)..(154)
<223> OTHER INFORMATION: LW852

<400> SEQUENCE: 5

Asn Cys Thr Arg Pro Asn Asn Asn Thr Arg Lys Arg Ile Arg Ile Gln
1               5                   10                  15

Arg Gly Pro Gly Arg Ala Phe Val Thr Ile Gly Lys Ile Gly Asn Met
             20                  25                  30

Arg Gln Ala His Cys Asn Ile Ser Arg Ala Lys Trp Asn Asn Thr Leu
        35                  40                  45

Lys Gln Ile Ala Ser Lys Leu Arg Glu Gln Phe Gly Asn Asn Lys Thr
    50                  55                  60
```

```
Ile Ile Phe Lys Gln Ser Ser Gly Gly Asp Pro Glu Ile Val Thr His
65                  70                  75                  80

Ser Phe Asn Cys Gly Gly Glu Phe Phe Tyr Cys Asn Ser Thr Gln Leu
                85                  90                  95

Phe Asn Ser Thr Trp Phe Asn Ser Thr Trp Ser Thr Glu Gly Ser Asn
            100                 105                 110

Asn Thr Glu Gly Ser Asp Thr Ile Thr Leu Pro Cys Arg Ile Lys Gln
        115                 120                 125

Ile Ile Asn Met Trp Gln Glu Val Gly Lys Ala Met Tyr Ala Pro Pro
    130                 135                 140

Ile Ser Gly Gln Ile Arg Cys Ser Ser Asn
145                 150


<210> SEQ ID NO 6
<211> LENGTH: 154
<212> TYPE: PRT
<213> ORGANISM: Human immunodeficiency virus type 1
<220> FEATURE:
<221> NAME/KEY: MISC_FEATURE
<222> LOCATION: (1)..(154)
<223> OTHER INFORMATION: wt1

<400> SEQUENCE: 6

Asn Cys Thr Arg Pro Asn Asn Asn Thr Arg Lys Lys Ile Arg Ile Gln
1               5                   10                  15

Arg Gly Pro Gly Arg Ala Phe Val Thr Ile Gly Lys Ile Gly Asn Met
            20                  25                  30

Arg Gln Ala His Cys Asn Ile Ser Arg Ala Lys Trp Asn Ala Thr Leu
        35                  40                  45

Lys Gln Ile Ala Ser Lys Leu Arg Glu Gln Phe Gly Asn Asn Lys Thr
    50                  55                  60

Ile Ile Phe Lys Gln Ser Ser Gly Gly Asp Pro Glu Ile Val Thr His
65                  70                  75                  80

Ser Phe Asn Cys Gly Gly Glu Phe Phe Tyr Cys Asn Ser Thr Gln Leu
                85                  90                  95

Phe Asn Ser Thr Trp Phe Asn Ser Thr Trp Ser Thr Glu Gly Ser Asn
            100                 105                 110

Asn Thr Glu Gly Ser Asp Thr Ile Thr Leu Pro Cys Arg Ile Lys Gln
        115                 120                 125

Ile Ile Asn Met Trp Gln Glu Val Gly Lys Ala Met Tyr Ala Pro Pro
    130                 135                 140

Ile Ser Gly Gln Ile Arg Cys Ser Ser Asn
145                 150


<210> SEQ ID NO 7
<211> LENGTH: 154
<212> TYPE: PRT
<213> ORGANISM: Human immunodeficiency virus type 1
<220> FEATURE:
<221> NAME/KEY: MISC_FEATURE
<222> LOCATION: (1)..(154)
<223> OTHER INFORMATION: MCK1

<400> SEQUENCE: 7

Asn Cys Thr Arg Pro Asn Asn Asn Thr Arg Lys Arg Ile Arg Ile Gln
1               5                   10                  15

Arg Gly Pro Gly Arg Ala Phe Val Thr Ile Gly Lys Ile Gly Asn Met
            20                  25                  30

Arg Gln Ala His Cys Asn Ile Ser Arg Ala Lys Trp Asn Ala Thr Leu
        35                  40                  45
```

```
Lys Gln Ile Ala Ser Lys Leu Arg Glu Gln Phe Gly Asn Asn Lys Thr
    50                  55                  60

Ile Ile Phe Lys Gln Ser Ser Gly Gly Asp Pro Glu Ile Val Thr His
65                  70                  75                  80

Ser Phe Asn Cys Gly Gly Glu Phe Phe Tyr Cys Asn Ser Thr Gln Leu
                85                  90                  95

Phe Asn Ser Thr Trp Phe Asn Ser Thr Trp Ser Thr Glu Gly Ser Asn
            100                 105                 110

Asn Thr Glu Gly Ser Asp Thr Ile Thr Leu Pro Cys Arg Ile Lys Gln
        115                 120                 125

Phe Ile Asn Met Trp Gln Glu Val Gly Lys Ala Met Tyr Ala Pro Pro
    130                 135                 140

Ile Ser Gly Gln Ile Arg Cys Ser Ser Asn
145                 150


<210> SEQ ID NO 8
<211> LENGTH: 154
<212> TYPE: PRT
<213> ORGANISM: Human immunodeficiency virus type 1
<220> FEATURE:
<221> NAME/KEY: MISC_FEATURE
<222> LOCATION: (1)..(154)
<223> OTHER INFORMATION: CH69-2

<400> SEQUENCE: 8

Asn Cys Thr Arg Pro Asn Asn Asn Thr Arg Lys Lys Ile Arg Ile Gln
1               5                   10                  15

Arg Gly Pro Gly Arg Ala Phe Val Thr Ile Gly Lys Ile Gly Asn Met
            20                  25                  30

Arg Gln Ala His Cys Asn Ile Ser Arg Ala Lys Trp Asn Ala Thr Leu
        35                  40                  45

Lys Gln Ile Ala Ser Lys Leu Arg Glu Gln Phe Gly Asn Asn Lys Thr
    50                  55                  60

Ile Ile Phe Lys Gln Ser Ser Gly Gly Asp Pro Glu Ile Val Thr His
65                  70                  75                  80

Ser Phe Asn Cys Gly Gly Glu Phe Phe Tyr Cys Asn Ser Thr Gln Leu
                85                  90                  95

Phe Asn Ser Thr Trp Phe Asn Ser Thr Trp Ser Thr Glu Gly Ser Asn
            100                 105                 110

Asn Thr Glu Gly Ser Asp Thr Ile Thr Leu Pro Cys Arg Ile Lys Gln
        115                 120                 125

Ile Ile Asn Met Trp Gln Glu Val Gly Lys Ala Met Tyr Ala Pro Pro
    130                 135                 140

Ile Ser Gly Gln Ile Arg Cys Ser Ser Asn
145                 150


<210> SEQ ID NO 9
<211> LENGTH: 154
<212> TYPE: PRT
<213> ORGANISM: Human immunodeficiency virus type 1
<220> FEATURE:
<221> NAME/KEY: MISC_FEATURE
<222> LOCATION: (1)..(154)
<223> OTHER INFORMATION: XB3

<400> SEQUENCE: 9

Asn Cys Thr Arg Pro Asn Asn Asn Thr Arg Lys Lys Ile Arg Ile Gln
1               5                   10                  15

Arg Gly Pro Gly Arg Ala Phe Val Thr Ile Gly Lys Ile Gly Asn Met
```

```
            20                  25                  30

Arg Gln Ala His Cys Asn Ile Ser Arg Ala Lys Trp Asn Ala Thr Leu
        35                  40                  45

Lys Gln Ile Ala Ser Lys Leu Arg Glu Gln Phe Gly Asn Asn Lys Thr
    50                  55                  60

Ile Ile Phe Lys Gln Ser Ser Gly Gly Asp Pro Glu Ile Val Thr His
65                  70                  75                  80

Ser Phe Asn Cys Gly Gly Glu Phe Phe Tyr Cys Asn Ser Thr Gln Leu
                85                  90                  95

Phe Asn Ser Thr Trp Phe Asn Ser Thr Trp Ser Thr Glu Gly Ser Asn
            100                 105                 110

Asn Thr Glu Gly Ser Asp Thr Ile Thr Leu Pro Cys Arg Ile Lys Gln
        115                 120                 125

Phe Ile Asn Met Trp Gln Glu Val Gly Lys Ala Met Tyr Ala Pro Pro
    130                 135                 140

Ile Ser Gly Gln Ile Arg Cys Ser Ser Asn
145                 150


<210> SEQ ID NO 10
<211> LENGTH: 154
<212> TYPE: PRT
<213> ORGANISM: Human immunodeficiency virus type 1
<220> FEATURE:
<221> NAME/KEY: MISC_FEATURE
<222> LOCATION: (1)..(154)
<223> OTHER INFORMATION: wt2

<400> SEQUENCE: 10

Asn Cys Thr Arg Pro Asn Asn Asn Thr Arg Lys Lys Ile Arg Ile Gln
1               5                   10                  15

Arg Gly Pro Gly Arg Ala Phe Val Thr Ile Gly Lys Ile Gly Asn Met
            20                  25                  30

Arg Gln Ala His Cys Asn Ile Ser Arg Ala Lys Trp Asn Ala Thr Leu
        35                  40                  45

Lys Gln Ile Asp Ser Lys Leu Arg Glu Gln Phe Gly Asn Asn Lys Thr
    50                  55                  60

Ile Ile Phe Lys Gln Ser Ser Gly Gly Asp Pro Glu Ile Val Thr His
65                  70                  75                  80

Ser Phe Asn Cys Gly Gly Glu Phe Phe Tyr Cys Asn Ser Thr Gln Leu
                85                  90                  95

Phe Asn Ser Thr Trp Phe Asn Ser Thr Trp Ser Thr Glu Gly Ser Asn
            100                 105                 110

Asn Thr Glu Gly Ser Asp Thr Ile Thr Leu Pro Cys Arg Ile Lys Gln
        115                 120                 125

Ile Ile Asn Met Trp Gln Glu Val Gly Lys Ala Met Tyr Ala Pro Pro
    130                 135                 140

Ile Ser Gly Gln Ile Arg Cys Ser Ser Asn
145                 150


<210> SEQ ID NO 11
<211> LENGTH: 154
<212> TYPE: PRT
<213> ORGANISM: Human immunodeficiency virus type 1
<220> FEATURE:
<221> NAME/KEY: MISC_FEATURE
<222> LOCATION: (1)..(154)
<223> OTHER INFORMATION: LW12.3

<400> SEQUENCE: 11
```

-continued

```
Asn Cys Thr Arg Pro Asn Asn Asn Thr Arg Lys Arg Ile Arg Ile Gln
1               5                   10                  15

Arg Gly Pro Gly Arg Thr Phe Val Thr Ile Gly Lys Ile Gly Asn Met
            20                  25                  30

Arg Gln Ala His Cys Asn Ile Ser Arg Ala Lys Trp Asn Asn Thr Leu
        35                  40                  45

Lys Gln Ile Ala Ser Lys Leu Arg Glu Gln Tyr Gly Asn Asn Lys Thr
    50                  55                  60

Ile Ile Phe Lys Gln Ser Ser Gly Gly Asp Leu Glu Ile Val Thr His
65                  70                  75                  80

Ser Phe Asn Cys Gly Gly Glu Phe Phe Tyr Cys Asn Ser Thr Gln Leu
                85                  90                  95

Phe Asn Ser Thr Trp Phe Asn Ser Thr Trp Ser Thr Glu Gly Ser Asn
            100                 105                 110

Asn Thr Glu Gly Ser Asp Thr Ile Thr Leu Pro Cys Arg Ile Lys Gln
        115                 120                 125

Ile Ile Asn Met Trp Gln Glu Val Gly Lys Ala Met Tyr Ala Pro Pro
    130                 135                 140

Ile Ser Gly Gln Ile Arg Cys Ser Ser Asn
145                 150


<210> SEQ ID NO 12
<211> LENGTH: 154
<212> TYPE: PRT
<213> ORGANISM: Human immunodeficiency virus type 1
<220> FEATURE:
<221> NAME/KEY: MISC_FEATURE
<222> LOCATION: (1)..(154)
<223> OTHER INFORMATION: BH10

<400> SEQUENCE: 12

Asn Cys Thr Arg Pro Asn Asn Asn Thr Arg Lys Ser Ile Arg Ile Gln
1               5                   10                  15

Arg Gly Pro Gly Arg Ala Phe Val Thr Ile Gly Lys Ile Gly Asn Met
            20                  25                  30

Arg Gln Ala His Cys Asn Ile Ser Arg Ala Lys Trp Asn Asn Thr Leu
        35                  40                  45

Lys Gln Ile Asp Ser Lys Leu Arg Glu Gln Phe Gly Asn Asn Lys Thr
    50                  55                  60

Ile Ile Phe Lys Gln Ser Ser Gly Gly Asp Pro Glu Ile Val Thr His
65                  70                  75                  80

Ser Phe Asn Cys Gly Gly Glu Phe Phe Tyr Cys Asn Ser Thr Gln Leu
                85                  90                  95

Phe Asn Ser Thr Trp Phe Asn Ser Thr Trp Ser Thr Lys Gly Ser Asn
            100                 105                 110

Asn Thr Glu Gly Ser Asp Thr Ile Thr Leu Pro Cys Arg Ile Lys Gln
        115                 120                 125

Ile Ile Asn Met Trp Gln Glu Val Gly Lys Ala Met Tyr Ala Pro Pro
    130                 135                 140

Ile Ser Gly Gln Ile Arg Cys Ser Ser Asn
145                 150


<210> SEQ ID NO 13
<211> LENGTH: 154
<212> TYPE: PRT
<213> ORGANISM: Human immunodeficiency virus type 1
<220> FEATURE:
<221> NAME/KEY: MISC_FEATURE
<222> LOCATION: (1)..(154)
```

<223> OTHER INFORMATION: PV22

<400> SEQUENCE: 13

```
Asn Cys Thr Arg Pro Asn Asn Asn Thr Arg Lys Ser Ile Arg Ile Gln
1               5                   10                  15

Arg Gly Pro Gly Arg Ala Phe Val Thr Ile Gly Lys Ile Gly Asn Met
            20                  25                  30

Arg Gln Ala His Cys Asn Ile Ser Arg Ala Lys Trp Asn Asn Thr Leu
        35                  40                  45

Lys Gln Ile Asp Ser Lys Leu Arg Glu Gln Phe Gly Asn Asn Lys Thr
    50                  55                  60

Ile Ile Phe Lys Gln Ser Ser Gly Gly Asp Pro Glu Ile Val Thr His
65                  70                  75                  80

Ser Phe Asn Cys Gly Gly Glu Phe Phe Tyr Cys Asn Ser Thr Gln Leu
                85                  90                  95

Phe Asn Ser Thr Trp Phe Asn Ser Thr Trp Ser Thr Glu Gly Ser Asn
            100                 105                 110

Asn Thr Glu Gly Ser Asp Thr Ile Thr Leu Pro Cys Arg Ile Lys Gln
        115                 120                 125

Phe Ile Asn Met Trp Gln Glu Val Gly Lys Ala Met Tyr Ala Pro Pro
    130                 135                 140

Ile Ser Gly Gln Ile Arg Cys Ser Ser Asn
145                 150
```

<210> SEQ ID NO 14
<211> LENGTH: 154
<212> TYPE: PRT
<213> ORGANISM: Human immunodeficiency virus type 1
<220> FEATURE:
<221> NAME/KEY: MISC_FEATURE
<222> LOCATION: (1)..(154)
<223> OTHER INFORMATION: BRU

<400> SEQUENCE: 14

```
Asn Cys Thr Arg Pro Asn Asn Asn Thr Arg Lys Ser Ile Arg Ile Gln
1               5                   10                  15

Arg Gly Pro Gly Arg Ala Phe Val Thr Ile Gly Lys Ile Gly Asn Met
            20                  25                  30

Arg Gln Ala His Cys Asn Ile Ser Arg Ala Lys Trp Asn Ala Thr Leu
        35                  40                  45

Lys Gln Ile Ala Ser Lys Leu Arg Glu Gln Phe Gly Asn Asn Lys Thr
    50                  55                  60

Ile Ile Phe Lys Gln Ser Ser Gly Gly Asp Pro Glu Ile Val Thr His
65                  70                  75                  80

Ser Phe Asn Cys Gly Gly Glu Phe Phe Tyr Cys Asn Ser Thr Gln Leu
                85                  90                  95

Phe Asn Ser Thr Trp Phe Asn Ser Thr Trp Ser Thr Glu Gly Ser Asn
            100                 105                 110

Asn Thr Glu Gly Ser Asp Thr Ile Thr Leu Pro Cys Arg Ile Lys Gln
        115                 120                 125

Phe Ile Asn Met Trp Gln Glu Val Gly Lys Ala Met Tyr Ala Pro Pro
    130                 135                 140

Ile Ser Gly Gln Ile Arg Cys Ser Ser Asn
145                 150
```

<210> SEQ ID NO 15
<211> LENGTH: 154
<212> TYPE: PRT

```
<213> ORGANISM: Human immunodeficiency virus type 1
<220> FEATURE:
<221> NAME/KEY: MISC_FEATURE
<222> LOCATION: (1)..(154)
<223> OTHER INFORMATION: CH69-7

<400> SEQUENCE: 15

Asn Cys Thr Arg Pro Asn Asn Asn Thr Arg Lys Lys Ile Arg Ile Gln
1               5                   10                  15

Arg Gly Pro Gly Arg Ala Phe Val Thr Leu Gly Lys Ile Gly Asn Met
            20                  25                  30

Arg Gln Ala His Cys Asn Ile Ser Arg Ala Lys Trp Asn Ala Thr Leu
        35                  40                  45

Lys Gln Ile Ala Ser Lys Leu Arg Glu Gln Phe Gly Ser Asn Lys Thr
    50                  55                  60

Ile Ile Phe Lys Gln Ser Ser Gly Gly Asp Pro Glu Ile Val Thr His
65                  70                  75                  80

Ser Phe Asn Cys Gly Gly Glu Phe Phe Tyr Cys Asn Ser Thr Gln Leu
                85                  90                  95

Phe Asn Ser Thr Trp Phe Asn Ser Thr Trp Ser Thr Glu Gly Ser Asn
            100                 105                 110

Asn Thr Glu Gly Ser Asp Thr Ile Thr Leu Pro Cys Arg Ile Lys Gln
        115                 120                 125

Ile Ile Asn Met Trp Gln Glu Val Gly Lys Ala Met Tyr Ala Pro Pro
    130                 135                 140

Ile Ser Gly Gln Ile Arg Cys Ser Ser Asn
145                 150


<210> SEQ ID NO 16
<211> LENGTH: 154
<212> TYPE: PRT
<213> ORGANISM: Human immunodeficiency virus type 1
<220> FEATURE:
<221> NAME/KEY: MISC_FEATURE
<222> LOCATION: (1)..(154)
<223> OTHER INFORMATION: 1H6

<400> SEQUENCE: 16

Asn Cys Thr Arg Pro Asn Asn Asn Thr Arg Lys Lys Ile Arg Ile Gln
1               5                   10                  15

Arg Gly Pro Gly Arg Thr Phe Val Thr Ile Gly Lys Ile Gly Asn Met
            20                  25                  30

Arg Gln Ala His Cys Asn Ile Ser Arg Ala Lys Trp Asn Ala Thr Leu
        35                  40                  45

Lys Gln Ile Asp Ser Lys Leu Arg Glu Gln Phe Gly Asn Asn Lys Thr
    50                  55                  60

Ile Ile Phe Lys Gln Ser Ser Gly Gly Asp Pro Glu Ile Val Thr His
65                  70                  75                  80

Ser Phe Asn Cys Gly Gly Glu Phe Phe Tyr Cys Asn Ser Thr Gln Leu
                85                  90                  95

Phe Asn Ser Thr Trp Phe Asn Ser Thr Trp Ser Thr Glu Gly Ser Asn
            100                 105                 110

Asn Thr Glu Gly Ser Asp Thr Ile Thr Leu Pro Cys Arg Ile Lys Gln
        115                 120                 125

Ile Ile Asn Met Trp Gln Glu Val Gly Lys Ala Met Tyr Ala Pro Pro
    130                 135                 140

Ile Ser Gly Gln Ile Arg Cys Ser Ser Asn
145                 150
```

<210> SEQ ID NO 17
<211> LENGTH: 154
<212> TYPE: PRT
<213> ORGANISM: Human immunodeficiency virus type 1
<220> FEATURE:
<221> NAME/KEY: MISC_FEATURE
<222> LOCATION: (1)..(154)
<223> OTHER INFORMATION: 1F8

<400> SEQUENCE: 17

```
Asn Cys Thr Arg Pro Asn Asn Asn Thr Arg Lys Lys Ile Arg Ile Gln
1               5                   10                  15

Arg Gly Pro Gly Arg Ala Leu Val Thr Ile Gly Lys Ile Gly Asn Met
            20                  25                  30

Arg Gln Ala His Cys Asn Ile Ser Arg Ala Lys Trp Asn Ala Thr Leu
        35                  40                  45

Lys Gln Ile Asp Ser Lys Leu Arg Glu Gln Phe Gly Asn Asn Lys Thr
    50                  55                  60

Ile Ile Phe Lys Gln Ser Ser Gly Gly Asp Pro Glu Ile Val Thr His
65                  70                  75                  80

Ser Phe Asn Cys Gly Gly Glu Phe Phe Tyr Cys Asn Ser Thr Gln Leu
                85                  90                  95

Phe Asn Ser Thr Trp Phe Asn Ser Thr Trp Ser Thr Glu Gly Ser Asn
            100                 105                 110

Asn Thr Glu Gly Ser Asp Thr Ile Thr Leu Pro Cys Arg Ile Lys Gln
        115                 120                 125

Ile Ile Asn Met Trp Gln Glu Val Gly Lys Ala Met Tyr Ala Pro Pro
    130                 135                 140

Ile Ser Gly Gln Ile Arg Cys Ser Ser Asn
145                 150
```

<210> SEQ ID NO 18
<211> LENGTH: 154
<212> TYPE: PRT
<213> ORGANISM: Human immunodeficiency virus type 1
<220> FEATURE:
<221> NAME/KEY: MISC_FEATURE
<222> LOCATION: (1)..(154)
<223> OTHER INFORMATION: mfA

<400> SEQUENCE: 18

```
Asn Cys Thr Arg Pro Asn Asn Asn Thr Arg Lys Ser Ile Arg Ile Gln
1               5                   10                  15

Arg Gly Pro Gly Arg Ala Phe Val Thr Ile Gly Lys Ile Gly Asn Met
            20                  25                  30

Arg Gln Ala His Cys Asn Ile Ser Arg Ala Lys Trp Met Ser Thr Leu
        35                  40                  45

Lys Gln Ile Ala Ser Lys Leu Arg Glu Gln Phe Gly Asn Asn Lys Thr
    50                  55                  60

Val Ile Phe Lys Gln Ser Ser Gly Gly Asp Pro Glu Ile Val Thr His
65                  70                  75                  80

Ser Phe Asn Cys Gly Gly Glu Phe Phe Tyr Cys Asn Ser Thr Gln Leu
                85                  90                  95

Phe Asn Ser Thr Trp Phe Asn Ser Thr Trp Ser Thr Glu Gly Ser Asn
            100                 105                 110

Asn Thr Glu Gly Ser Asp Thr Ile Thr Leu Pro Cys Arg Ile Lys Gln
        115                 120                 125

Phe Ile Asn Met Trp Gln Glu Val Gly Lys Ala Met Tyr Ala Pro Pro
    130                 135                 140
```

Ile Ser Gly Gln Ile Arg Cys Ser Ser Asn
145 150

<210> SEQ ID NO 19
<211> LENGTH: 154
<212> TYPE: PRT
<213> ORGANISM: Human immunodeficiency virus type 1
<220> FEATURE:
<221> NAME/KEY: MISC_FEATURE
<222> LOCATION: (1)..(154)
<223> OTHER INFORMATION: CH69-6

<400> SEQUENCE: 19

Asn Cys Ile Arg Pro Asn Asn Asn Thr Arg Lys Lys Ile Arg Ile Gln
1 5 10 15

Arg Gly Pro Gly Arg Ala Leu Val Thr Ile Gly Lys Ile Gly Asn Met
20 25 30

Arg Gln Ala His Cys Asn Ile Ser Arg Ala Lys Trp Asn Ala Thr Leu
35 40 45

Lys Gln Ile Ala Ser Lys Leu Arg Glu Gln Phe Gly Asn Asn Lys Thr
50 55 60

Ile Ile Phe Lys Gln Ser Ser Gly Gly Asp Pro Glu Ile Val Thr His
65 70 75 80

Ser Phe Asn Cys Gly Gly Glu Phe Phe Tyr Cys Asn Ser Thr Gln Leu
85 90 95

Phe Asn Ser Thr Trp Phe Asn Ser Thr Trp Ser Thr Glu Gly Ser Asn
100 105 110

Asn Ala Glu Gly Ser Asp Thr Ile Thr Leu Pro Cys Arg Ile Lys Gln
115 120 125

Ile Ile Asn Met Trp Gln Glu Val Gly Lys Ala Met Tyr Ala Pro Pro
130 135 140

Ile Ser Gly Gln Ile Arg Cys Ser Ser Asn
145 150

<210> SEQ ID NO 20
<211> LENGTH: 154
<212> TYPE: PRT
<213> ORGANISM: Human immunodeficiency virus type 1
<220> FEATURE:
<221> NAME/KEY: MISC_FEATURE
<222> LOCATION: (1)..(154)
<223> OTHER INFORMATION: CH69-5

<400> SEQUENCE: 20

Asn Cys Ile Arg Pro Asn Asn Asn Thr Arg Lys Lys Ile Arg Ile Gln
1 5 10 15

Arg Gly Pro Gly Arg Ala Leu Val Thr Ile Gly Lys Ile Gly Asn Met
20 25 30

Arg Gln Ala His Cys Asn Ile Ser Arg Ala Lys Trp Asn Ala Thr Leu
35 40 45

Lys Gln Ile Ala Ser Lys Leu Arg Glu Gln Phe Gly Asn Asn Lys Thr
50 55 60

Ile Ile Phe Lys Gln Ser Ser Gly Gly Asp Pro Glu Ile Val Thr His
65 70 75 80

Ser Phe Asn Cys Gly Gly Glu Phe Phe Tyr Cys Asn Ser Thr Gln Leu
85 90 95

Phe Asn Ser Thr Trp Phe Asn Ser Thr Trp Ser Thr Glu Gly Ser Asn
100 105 110

Asn Ala Glu Gly Ser Asp Thr Ile Thr Leu Pro Cys Arg Ile Lys Gln

```
        115                 120                 125

Ile Ile Asn Met Trp Gln Glu Val Gly Lys Ala Met Tyr Ala Pro Pro
    130                 135                 140

Ile Ser Gly Gln Ile Arg Cys Ser Ser Asn
145                 150


<210> SEQ ID NO 21
<211> LENGTH: 154
<212> TYPE: PRT
<213> ORGANISM: Human immunodeficiency virus type 1
<220> FEATURE:
<221> NAME/KEY: MISC_FEATURE
<222> LOCATION: (1)..(154)
<223> OTHER INFORMATION: 1B6

<400> SEQUENCE: 21

Asn Cys Thr Arg Pro Asn Asn Asn Thr Arg Lys Lys Ile Arg Ile Gln
1               5                   10                  15

Arg Gly Pro Gly Arg Thr Phe Asp Thr Ile Gly Lys Ile Gly Asn Met
            20                  25                  30

Arg Gln Ala His Cys Asn Ile Ser Arg Ala Lys Trp Asn Ala Thr Leu
        35                  40                  45

Lys Gln Ile Asp Ser Lys Leu Arg Glu Gln Phe Gly Asn Asn Lys Thr
    50                  55                  60

Ile Ile Phe Lys Gln Ser Ser Gly Gly Asp Pro Glu Ile Val Thr His
65                  70                  75                  80

Ser Phe Asn Cys Gly Gly Glu Phe Phe Tyr Cys Asn Ser Thr Gln Leu
                85                  90                  95

Phe Asn Ser Thr Trp Phe Asn Ser Thr Trp Ser Thr Glu Gly Ser Asn
            100                 105                 110

Asn Thr Glu Gly Ser Asp Thr Ile Thr Leu Pro Cys Arg Ile Lys Gln
        115                 120                 125

Ile Ile Asn Met Trp Gln Glu Val Gly Lys Ala Met Tyr Ala Pro Pro
    130                 135                 140

Ile Ser Gly Gln Ile Arg Cys Ser Ser Asn
145                 150


<210> SEQ ID NO 22
<211> LENGTH: 154
<212> TYPE: PRT
<213> ORGANISM: Human immunodeficiency virus type 1
<220> FEATURE:
<221> NAME/KEY: MISC_FEATURE
<222> LOCATION: (1)..(154)
<223> OTHER INFORMATION: CH69-1

<400> SEQUENCE: 22

Asn Cys Ala Arg Pro Asn Asn Asn Thr Arg Lys Lys Ile Arg Ile Arg
1               5                   10                  15

Arg Gly Pro Gly Arg Ala Phe Val Thr Ile Gly Lys Ile Gly Asn Met
            20                  25                  30

Arg Gln Ala His Cys Asn Ile Ser Arg Ala Lys Trp Asn Ala Thr Leu
        35                  40                  45

Lys Gln Ile Ala Ser Lys Leu Arg Glu Gln Phe Gly Asn Asn Lys Thr
    50                  55                  60

Ile Ile Phe Lys Gln Ser Ser Gly Gly Asp Pro Glu Ile Val Ala His
65                  70                  75                  80

Ser Phe Asn Cys Gly Gly Glu Phe Phe Tyr Cys Asn Ser Thr Gln Leu
                85                  90                  95
```

```
Phe Asn Ser Thr Trp Phe Asn Ser Thr Trp Ser Thr Glu Gly Ser Asn
            100                 105                 110

Asn Thr Glu Gly Ser Asp Thr Ile Thr Leu Pro Cys Arg Ile Lys Gln
        115                 120                 125

Ile Ile Asn Met Trp Gln Glu Val Gly Lys Ala Met Tyr Ala Pro Pro
    130                 135                 140

Ile Ser Gly Gln Ile Arg Cys Ser Ser Asn
145                 150


<210> SEQ ID NO 23
<211> LENGTH: 154
<212> TYPE: PRT
<213> ORGANISM: Human immunodeficiency virus type 1
<220> FEATURE:
<221> NAME/KEY: MISC_FEATURE
<222> LOCATION: (1)..(154)
<223> OTHER INFORMATION: TH4-7-5

<400> SEQUENCE: 23

Asn Cys Thr Arg Pro Asn Asn Asn Thr Arg Lys Lys Phe Arg Ile Gln
1               5                   10                  15

Arg Gly Pro Gly Arg Ala Phe Val Thr Ile Gly Lys Ile Gly Asn Met
            20                  25                  30

Arg Gln Ala His Cys Asn Ile Ser Arg Ala Lys Trp Asn Ala Thr Leu
        35                  40                  45

Lys Gln Ile Ala Ser Lys Leu Arg Glu Gln Phe Gly Asn Asn Lys Thr
    50                  55                  60

Ile Ile Phe Lys Gln Ser Ser Gly Gly Asp Pro Glu Ile Val Thr His
65                  70                  75                  80

Ser Phe Asn Cys Gly Gly Glu Phe Phe Tyr Cys Asn Ser Thr Gln Leu
                85                  90                  95

Phe Asn Ser Thr Trp Ser Asn Ser Thr Leu Ser Thr Glu Gly Ser Asn
            100                 105                 110

Asn Thr Glu Gly Ser Asp Thr Ile Thr Leu Pro Cys Arg Ile Lys Gln
        115                 120                 125

Ile Ile Asn Met Trp Gln Glu Val Gly Lys Ala Met Tyr Ala Pro Pro
    130                 135                 140

Ile Ser Gly Gln Ile Arg Cys Ser Ser Asn
145                 150


<210> SEQ ID NO 24
<211> LENGTH: 154
<212> TYPE: PRT
<213> ORGANISM: Human immunodeficiency virus type 1
<220> FEATURE:
<221> NAME/KEY: MISC_FEATURE
<222> LOCATION: (1)..(154)
<223> OTHER INFORMATION: Human immunodeficiency virus type 1 envelope
      glycoprotein gp160 gene

<400> SEQUENCE: 24

Asn Cys Thr Arg Pro Tyr Asn Asn Lys Arg Lys Ser Ile Arg Ile Gln
1               5                   10                  15

Arg Gly Pro Gly Arg Ala Phe Val Thr Ile Gly Lys Ile Gly Asn Met
            20                  25                  30

Arg Gln Ala His Cys Asn Ile Ser Arg Ala Lys Trp Asn Ala Thr Leu
        35                  40                  45

Lys Gln Ile Ala Ser Lys Leu Arg Glu Gln Phe Gly Asn Asn Lys Thr
    50                  55                  60

Ile Ile Phe Lys Gln Ser Ser Gly Gly Asp Pro Glu Ile Val Thr His
```

-continued

```
65                  70                  75                  80

Ser Phe Asn Cys Gly Gly Glu Phe Phe Tyr Cys Asn Ser Thr Gln Leu
                85                  90                  95

Phe Asn Ser Thr Trp Phe Asn Ser Thr Trp Ser Thr Glu Glu Ser Asn
            100                 105                 110

Ser Thr Glu Gly Ser Asp Thr Ile Thr Leu Pro Cys Arg Ile Lys Gln
        115                 120                 125

Phe Ile Asn Met Trp Gln Lys Val Gly Lys Ala Met Tyr Ala Pro Pro
    130                 135                 140

Ile Ser Gly Gln Ile Arg Cys Ser Ser Asn
145                 150
```

METHOD FOR THE DETECTION OF HUMAN IMMUNODEFICIENCY VIRUS ENVELOPE (HIV) GLYCOPROTEIN UTILIZING CARBOHYDRATE BINDING MODULE (CBM) 20 OR 21

FIELD OF THE INVENTION

The present invention relates to an antibody mimetic of carbohydrate binding module (CBM) which specifically binds to an epitope on HIV glycoprotein. The present invention also relates to a method of detecting HIV glycoprotein.

BACKGROUND OF THE INVENTION

Human immunodeficiency virus (HIV) is known to cause acquired immune deficiency syndrome (AIDS), and because the HIV exhibits rapid genetic drift, widely divergent strains are emerging. Thus, detection and treatment of variant strains have proven to be challenging and difficult.

The diagnosis of HIV infection is most commonly achieved by detecting antibody against HIV. Methods for laboratory diagnosis of HIV infection have evolved and offered a large number and a variety of effective methods that can prolong and improve the quality of life for HIV infected patients. In the industrialized countries, enzyme immunoassay (EIA) is the most commonly used method. The assay is comprised of an immobilized viral antigen, which may be comprised of viral lysate, retrovirus proteins or natural or synthetic polypeptides, that reacts with blood or serum components suspected of containing HIV antibodies. Although there is a window stage problem (limiting to the anti-HIV antibody generation time) for the EIA detection, it is still the most popular for HIV diagnosis due to excellent sensitivity, good specificity, and relatively lower cost.

However, there are some disadvantages of the use of isolated viral proteins as antigens for EIA method, such as: the need to grow and handle large quantities of live infectious virus; the possibility that the live virus might be incorporated into test materials; the variable nature of the resulting viral lysate; and the substantial number of false positive and false negative results that require additional confirmatory testing. The use of synthetic polypeptides, which can be engineered to immunologically mimic antigenic epitopes of HIV viruses, may avoid some of the above-mentioned disadvantages, but viral antigenic drift could result in the failure to detect HIV infected sera, presumably due to limited presentation of viral epitopes.

Therefore, there remains a need for a reliable, specific and sensitive test for HIV infection that is affordable and practical on a large scale.

There is also an urgent need to develop an effective prophylactic vaccine and other therapeutic strategies to limit HIV transmission as the epidemic continuous unabated. Most successful vaccines consist of either live-attenuated or inactivated viral particles. However, live-attenuation of the HIV-related simian immunodeficiency virus, resulting in protective responses without resulting pathogenicity has not been accomplished, raising safety concerns that make human trial intractable. Also, HIV has many sophisticated mechanisms to evade envelope glycoprotein-directed antibody responses efficiently, including shrouding well-conserved structures by glycan shielding and masking of vulnerable receptor-binding sites by conformational and steric constraints. Therefore, researches turned to envelope glycoprotein-based immunogens as a means of eliciting antibodies, but the use of monomeric gp120 or peptides derived from the immunodominant V3 loop of gp120 can not generate boardly used antibodies but type-specific antibodies.

As a result, the development of an effective detection and prophylactic vaccine against HIV remains an unrealized goal in the effort to contain the current pandemic.

SUMMARY OF THE INVENTION

The present invention provides an antibody mimetic of CBM family which specifically binds to an epitope on HIV glycoprotein. The present invention further provides a method of detecting HIV glycoprotein comprising: (a) introducing into contact with a solid surface to which is bound a known quantity of CBM capable of binding to HIV glycoprotein; (b) incubating sample in contact with said surface to form CBM-HIV glycoprotein complexes; and (c) incubating the complexes and subjecting sample to a labelled HIV antigen conjugate capable of yielding a quantitatively measurable signal to score sample as positive or negative for HIV-infection.

BRIEF DESCRIPTION OF THE DRAWINGS

FIG. 3 shows amino acid sequence alignment of the $V_H$ domain of 2G12 human monoclonal antibody (PDB ID: 1ZLS) with RoSBD (PDB ID: 2V8M).

FIGS. 8A and 8B show amino acid sequence alignment of 2G12 epitope regions of twenty one HIV1 isolates.

DETAILED DESCRIPTION OF THE INVENTION

The present invention provides an antibody mimetic of CBM which specifically binds to an epitope on HIV glycoprotein.

The term "CBM" used herein refers as a contiguous amino acid sequence within a carbohydrate-active enzyme with a discreet fold having carbohydrate-binding activity. In the primary structure classification of glycoside hydrolases, the CBMs are categorized into 53 families, which include several specificities such as cellulose, xylan, chitin, and starch binding.

The term "antibody mimetic" used herein refers to an object having similar function as the antibody in terms of binding against target structure, but its structure is simpler than an antibody. To produce a large amount of antibodies needs the following steps: (a) fusing single antibody-forming cells to tumor cells grown in culture. The resulting cell is called a hybridoma, (b) each hybridoma produces relatively large quantities of identical antibody molecules, and (c) allowing the hybridoma to multiply in culture, it is possible to produce a population of cells, each of which produces identical antibody molecules. It is labor-consuming and cost-consuming to make real antibodies; however, in the present invention, a broad range of host including bacteria, yeast, insect, and mammalian cells can be used to produce the antibody mimetic of CBM without using animals, which is simpler and more economic.

In the present invention, the preferable CBM is starch binding domain (SBD). The term "SBD" used herein refers to a functional domain that can bind granular or soluble starch, increasing the local concentration of substrate at the active site of the enzyme, and that may also disrupt the structure of the starch surface, thereby enhancing the amylolytic rate. At present, there are nine starch-binding CBM families: CBM20, CBM21, CBM25, CBM26, CBM34, CBM41, CBM45, CBM48 and CBM53. In a preferred embodiment of the invention, the SBD is the member of the CBM families 20 and 21, which is derived from *Aspergillus niger* glucoamylase (AnSBD) and *Rhizopus oryzae* glucoamylase (RoSBD), respectively. Even though CBM20 and CBM21 share fairly low identity in their amino acid sequences (approximately 13.5%), they have similar secondary and tertiary structures as well as the role in enhancing enzymatic activity in terms of hydrolyzing granular starch (Tung JY et al., Biochem. (2008) 416: 27-36).

The antibody mimetic of the present invention, wherein the RoSBD analyses by Glycan microarray screening shows that it has the ability to bind a glycan, Manα(1,2)Manα(1,2)Manα(1,2)Manα(1,3), which is a special glycan present in the epitope of the heavily glycosylated glycoprotein gp120 of HIV.

Figure 2A:
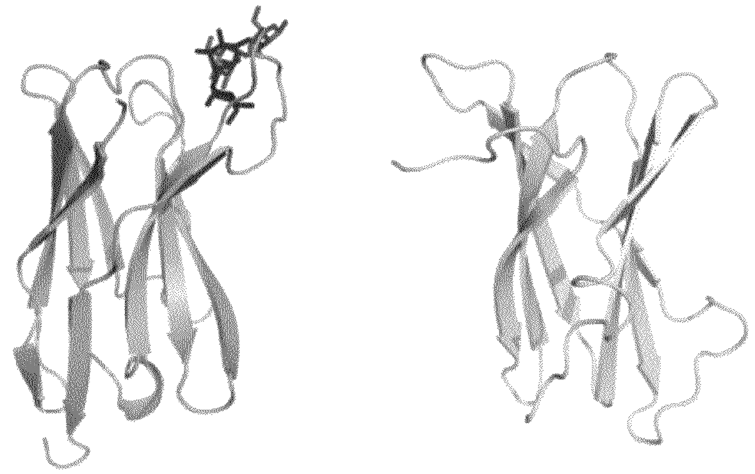
FIGS. 2A and 2B show structure modeling of the $V_H$ domain of 2G12 human monoclonal antibody (PDB ID: 1ZLS) with RoSBD (PDB ID: 2V8M).
Figure 2B:

Human monoclonal antibody 2G12 was first isolated and characterized at 1996, and proved to neutralize the clade A and B strains of HIV1 (Trkola A, et al., J. Virol. (1996) 70: 1100-1108). Site-directed alanine scanning mutagenesis has shown that the 2G12 epitope covers mainly on the high-mannose or hybrid glycans of residue N295, N332, N339, N386, N392, and N448 on gp120 (Sanders RW, et al., J. Virol. (2002) 76: 7293-7305 and Scanlan CN, et al., J. Virol. (2002) 76: 7306-7321), unlike most antibodies which recognize protein backbones of viral components. The crystal structure of 2G12 (PDB ID: 1ZLS) and its complexes with the oligosaccharide Man9GicNAc2 (PDB ID: 1OP5) reveal that two Fabs assemble into a VH domain-swapped dimer (Chalarese DA et al., Science (2003) 300: 2065-2071). In the present invention, the RoSBD and AnSBD also recognize glycan moieties of HIV. As FIGS. 2A and 2B shows, structure modeling of the VH domain of 2G12 human monoclonal antibody crystal (PDB ID: 1ZLS) and the RoSBD crystal complexed with glycan ligand (PDB ID: 2V8M) indicates that the _-sheet secondary structures are similar between these two proteins with a low root mean square deviation (RMSD) value. Furthermore, according the CATH: Protein Structure Classification database, it shows that the 2G12 human monoclonal antibody (PDB ID: 1ZLS) and the granular starch binding domain of *Aspergillus niger* glucoamylase belong to the same homologus superfamily (ID# 2.60.40.10), which is composed of the immunoglobulin-like proteins. Hence the structural similarity among RoSBD, AnSBD, and 2G12 may account for their functional similarity.

The present invention also provides a method of detecting HIV glycoprotein comprising: (a) introducing into contact with a solid surface to which is bound a known quantity of CBM capable of binding to HIV glycoprotein; (b) incubating sample in contact with said surface to form CBM-HIV glycoprotein complexes; and (c) incubating the complexes and subjecting same to a labelled HIV antigen conjugate which is capable of yielding a quantitatively measurable signal to score sample as positive or negative for HIV-infection. In a preferable embodiment, the CBM includes but is not limited to SBD. The method of the present invention, wherein said antigen of step (c) is labelled with an enzyme which is capable of producing the said signal when contact with an enzyme substrate. The enzyme comprises but not limited to horse radish peroxidase (HRP), alkali phosphatases, peroxidases, β-galactosidase, glucoamylase, urease and chloramphenicol acetyltransferase. In the preferable embodiment, the enzyme is HRP. Appropriate examples and the use of necessary substrates for the detection by means of enzymatic reactions are known to the person skilled in the art, and in the preferable embodiment, the substrate includes but is not limited to 3,3',5,5'-tetramethylbenzidibe (TMB).

Those skilled in the art will recognize the foregoing outline as a description of an ELISA procedure. They will recognize also that the generalized outline omits certain of the specific steps such as serial dilution and washing with appropriate buffers which are standard in the ELISA procedure. Although buffers and other reagents will be described hereinafter, and specific dilutions will be employed to illustrate the invention, the skilled artisan will recognize that these are illustrative only and that many equivalents are possible.

In the present invention, the major targets of the antibody mimetic are the exterior envelope glycoprotein of HIV, gp120 and the transmembrane glycoprotein, gp140. These proteins are generated by cleavage of a heavily glycosylated precursor protein, gp160, by furin-like enzymes during transport through the Golgi apparatus. Each new infectious cycle is initiated when the external envelope glycoprotein gp120 binds the primary receptor, CD4, which is embedded in the plasma membrane on the surface of potential target cells. In this invention, the antibody mimetic of CBM, which is not only can bind to the glycan structure of the envelope glycoprotein of HIV to serve as a potential therapeutic agent to block the interaction between HIV and target cells, but also can be a prophylactic vaccine against conserved but exposed epitopes on the HIV envelope glycoprotein to limit newly acquired infections.

As described above, the CBM has the ability to use as an antibody mimetic which can be applied to HIV detection and may further be applied as a prevention and treatment agent for HIV infection.

The examples below are non-limiting and are merely representative of various aspects and features of the present invention.

EXAMPLE

Example 1

Purification of RoSBD and AnSBD by Amylose Affinity Chromatography

The RoSBD and AnSBD were produced by *E. coli* system using pET23a and pET15Bb expression vector, respectively. The cell pellets of *E. coli* containing the recombinant protein was resuspended in binding buffer (50 mM sodium acetate, pH 5.5), and then homogenized (EmulsiFlex-05 homogenizer). The cell debris was removed by centrifugation at 16,000×g for 20 mM at 4° C., and the supernatant was subjected to purification by affinity chromatography equipped with amylose resin (New England Biolabs, Ipswich, Mass.). After the resin was washed with 5 column volumes of binding buffer, the supernatant was loaded to the column at a flow rate of 1 mL/min. The recombinant protein was then eluted by elution buffer (10 mM glycine/NaOH, pH 11.0) after the column was washed with another 5 column volumes of the binding buffer. The purified RoSBD/AnSBD was dialyzed against sodium acetate buffer (50 mM, pH 5.5) using an Amicon® Ultra-15 centrifugal filter devices (Millipore) PL-10 (10 kDa cutoff) after 30 kDa cutoff (Lin S C, et al., BMC Biochem. (2007) δ: 9-21 and Liu W T, et al., Biochem. Biophys. Res. Commun (2008) 377: 966-970).

Example 2

Glycan Array Screening of RoSBD

RoSBD was produced in *E. coli* system using pET23a expression vector and purified using amylose resin as previously described. Glycan microarray analyses were conducted by the Consortium for Functional Glycomics, Core H facility. The array contained a total of 377 different natural and synthetic glycans and version 3.1 was used for the analyses reported here. Briefly, RoSBD was diluted to 200 mg/mL in sodium acetate binding buffer (50 mM sodium acetate pH 5.5, 1% BSA and 0.05% Tween-20). Seventy microliters was applied to the printed surface of the array, coverslipped, and incubated at room temperature in a humidified chamber away from light for 1 hr. After the incubation, the coverslip was removed and rinsed four times in TSM buffer [50 mM Tris-HCI (pH 7.5), 10 mM MgCl2, and 0.5 M sucrose] and four times in TSM buffer. Seventy microliters of Anti-RoSBD monoclonal antibody, diluted to 1:200 in PBS binding buffer, was applied to the printed surface of the microarray and incubated in a humidified chamber for 1 hr. Washes were performed as above. To detect binding, the secondary antibody incubation was performed with Alexa488-labeled goat anti-mouse IgG at 5 mg/mL in PBS buffer for one hour in a humidified chamber, followed by wash steps. The binding image was read in a Perkin-Elmer Microarray XL4000 scanner and analyzed using Imagene (V.6) image analysis software.

Figure 1A:
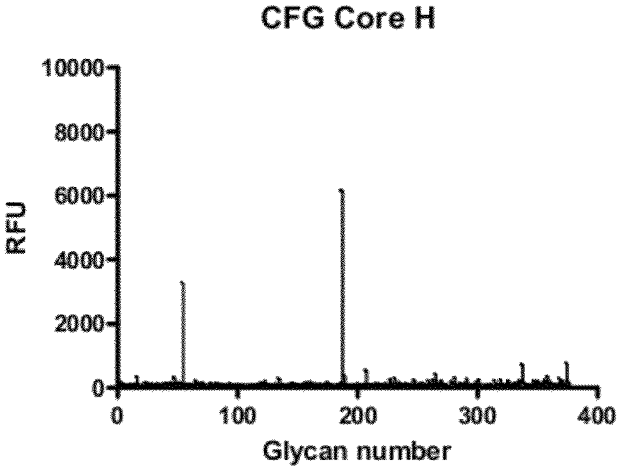
FIGS. 1A and 1B show glycan recognition of RoSBD determined by Glycan array analysis.
Figure 1B:
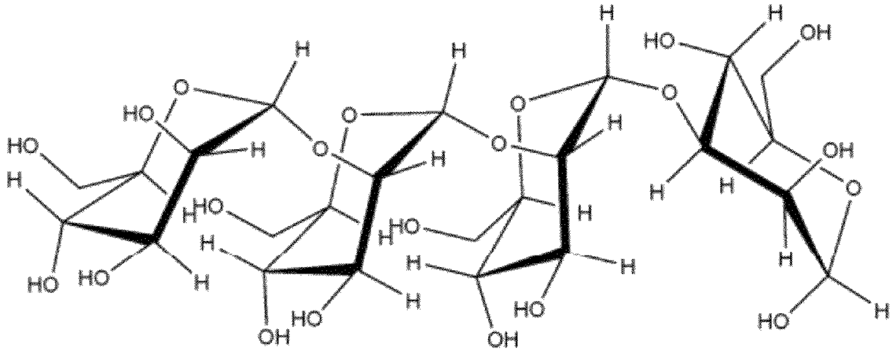

FIG. 1A illustrated the glycan array screening result of RoSBD. Among 377 different kinds of glycans, only Manα(1,2)Manα(1,2)Manα(1,2)Manα(1,3) (No. 187) showed evident interaction signal as indicated by the presence of the major peak. FIG. 1B showed the molecular structure of the special Manα(1,2)Manα(1,2)Manα(1,2)Manα(1,3) with the strongest signal. According to the analytical data provided by CFG Core H facility, most proteins with Manα(1,2)Manα(1,2)Manα(1,2)Manα(1,3) structure associated with human (*Homo Sapiens*) belong to human C-type Lectin family, such as Langerin (PDB ID: 3BC7), Mannose-binding protein/lectin (PDB ID: 1HUP) and Surfactant Protein D (PDB ID: 1PWB). Besides, a specific HIV1 neutralizing antibody 2G12 has also been characterized to recognize the Manα(1,2)Manα(1,2)Manα(1,2)Manα(1,3) structure of HIV1 glycoprotein gp120 (Wang J S, et al., Org. Biomol. Chem. (2007) δ: 1529-1540 and Pashov A, et al., Glycobiology (2005) 15: 994-1001). Therefore, whether RoSBD could bind to the HIV native antigen in HIV Ag & Ab positive panel was investigated employing sandwich ELISA.

Example 3

Structure Modeling and Sequence Alignment Between $V_H$ Domain of 2G12 and RoSBD FIGS. 2A and 2B showed the modeling result of the $V_H$ domain of 2G12 human monoclonal antibody (PDB ID: 1ZLS, left panel) and RoSBD (PDB ID: 2V8M, right panel). $V_H$ domain was located on the heavy chain of 2G12, and bound with N-linked glycans. Superimposition of both 2G12 and RoSBD structures indicated that the β-sheet secondary structures were similar between these two proteins, and most glycan ligand binding residues were localized in similar orientation (the RMSD value of structure comparison was 2.43 Å). It also proved the structure homology between RoSBD and a general antibody. Although the primary amino acid sequences of RoSBD and 2G12 possess only 8.9% identity, the structure-based alignment (as FIG. 3, SEQ ID NO: 1 and SEQ ID NO: 2 shown) revealed that high correlation between their key secondary structural elements (represented in gray zones) and ligand binding residues (represented in underlines).

Example 4

HIV-RoSBD Binding Analysis

The ELISA Procedure for Preparation of AnSBD/RoSBD Coated Plates

At first 100 μL of 100 nM AnSBD/RoSBD were coated on individual well of a 96-well plate (Greiner-Bio One GmbH, Frickenhausen, Germany) in sodium bicarbonate buffer (pH 9.5)/Tris-HCl buffer (pH 8) via 16-hr incubation at 4° C. The plate was washed with PBST [10 mM Phosphate Buffered Saline (pH 7.0) plus 0.05% Tween-20], then 200 μL blocking buffer [0.01 M Phosphate Buffered Saline (pH 7.0) plus 5% BSA] was added to each well and incubated at 37° C. for 2 hr. The blocking buffer was removed and the plate was dried at 25° C. for 1 hr. One hundred microliter per well of HIV Ag & Ab positive panel (ID# 9144532, SeraCare Life Sciences, Milford, Mass.) and Anti-HCV mixed titer performance panel (ID# PHV205-24, SeraCare Life Sciences, Milford, Mass.) was separately added and reacted at 37° C. for 1 hr. This HIV Ag & Ab positive panel was identified as HIV antigen positive by Perkin Elmer EIA and anti-HIV antibody positive by Abbott EIA. Secondly, HRP coupled *E. coli* HIV1 recombinant gp120 antigen conjugate (0.05 μg/mL) was added and reacted at 37° C. for 30 mM This conjugate could bind with the human anti-HIV1 antibody in HIV Ag & Ab positive panel directly. To test the specificity of the SBD binding to HIV, HCV test sample and HCV recombinant antigen (Core+NS3+NS5)-HRP conjugate (0.33 μg/mL) were analyzed following the same protocol in parallel. Finally, the plates were developed by adding 100 μL 3,3',5,5'-tetramethylbenzidibe (TMB) at 37° C. for 30 mM The absorbance was measured at 450 nm in ELISA reader after the reaction was stopped by addition of 100 μL 2 N $H_2SO_4$ in each well. These absorbance values were compiled as a statistical value (Cut off value; COV) and described in terms of cut off index (COI) value. The COV was calculated as the OD value of negative control (Normal Human Serum) plus 0.1 (COV=NC+0.1). The COI value was calculated as the OD value of test sample divided by COV. If a sample has an absorbance higher than the COV, i.e. COI value is greater than 1, it is considered to be positive in the assay.

Figure 4A:
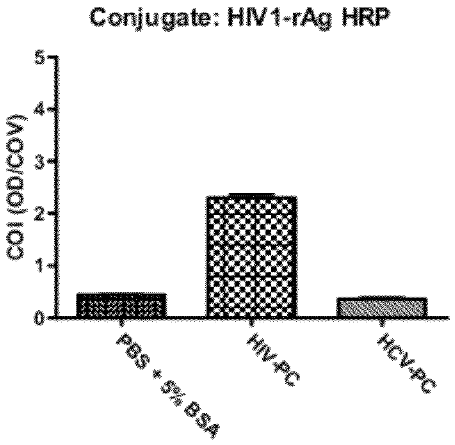
FIGS. 4A, 4B and 4C show HIV-RoSBD binding using HIV Ag & Ab positive panel #9144532.
Figure 4B:
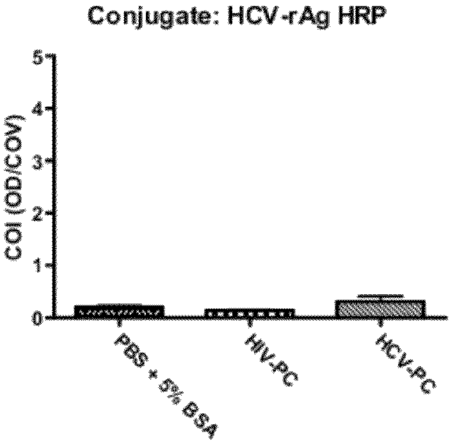
Figure 4C:
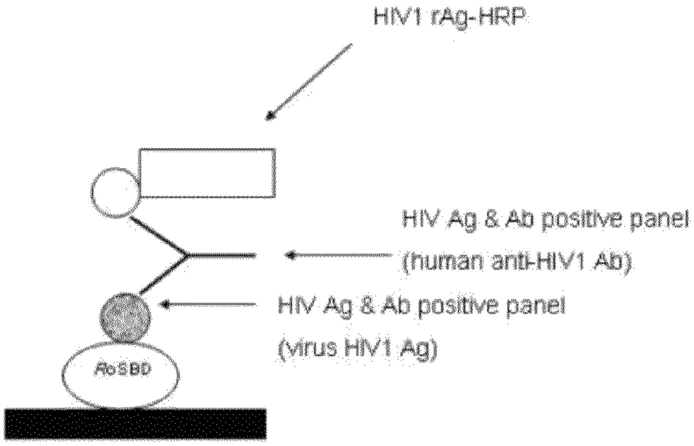

FIG. 4A revealed that the maximal COI value of RoSBD binding was 2.298 (HIV). Moreover, FIG. 4B demonstrated the specificity of the RoSBD employing Anti-HCV mixed titer performance panel. The difference was statistically significant (P<0.0001). These results indicated that RoSBD was specific in terms of binding to the HIV Ag & Ab positive panel, possibly the native HIV gp120 antigen glycoprotein.

Figure 5A:
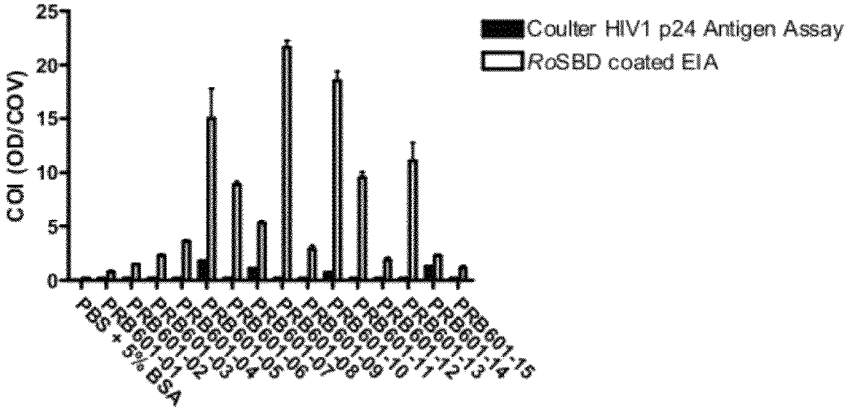
FIGS. 5A and 5B show HIV-RoSBD and HIV-AnSBD binding using HIV1 incidence/prevalence performance panel PRB601.
Figure 5B:
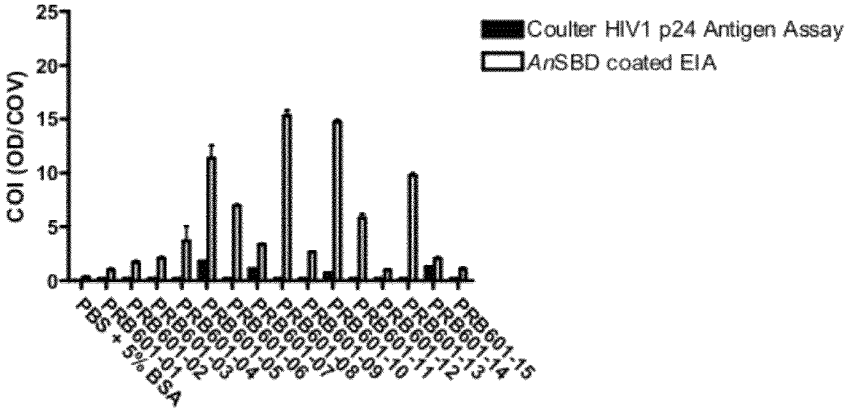

Furthermore, using the HIV1 incidence/prevalence performance panel PRB601 (SeraCare Life Sciences, Milford, Mass.) as the test sample, comparison of performance between RoSBD or AnSBD coated EIA and the Coulter HIV-1 p24 Antigen Assay was achieved. Specimens were undiluted aliquots from plasma units collected from HIV positive deferred plasma donors in the United States whose dates of infection and seroconverision were unknown. These specimens has been tested by Calypte anti-HIV1 Western blot assay and the result showed all fifteen members were anti-HIV1 p24 and gp160 antibody positive. FIGS. 5A and 5B revealed that the detection rate of the traditional HIV-1 p24 Antigen Assay was only 20.0%, whereas those of RoSBD coated EIA (93.3%) AnSBD coated EIA 86.7% were much higher.

Example 5

Glycan Effects on RoSBD/AnSBD Binding to HIV

Ten millimolar maltoheptaose (G7 glycan) and β-cyclodextrin (βCD) (Sigma-Aldrich, St. Louis, Mo.) were dissolved in PBS plus 5% BSA and mixed with the same volume of HIV Ag & Ab positive panel at 37° C. for 1 hr. After adding the mixture to RoSBD coated plate (100 nM in 0.05 M Tris-Hcl, pH 8) or AnSBD coated plate (100 nM in 0.05 M sodium bicarbonate buffer, pH 9.5) at 37° C. for 1 hr, 100 μL HRP coupled HIV1 recombinant gp120 antigen conjugate (0.05 μg/mL) was used for detection.

Figure 6A:
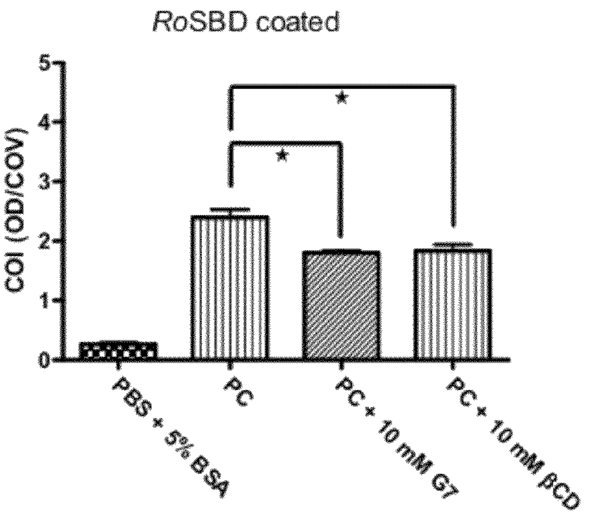
FIGS. 6A and 6B show competition of HIV-RoSBD and HIV-AnSBD binding by maltoheptaose (G7) and β-cyclodextrin (βCD).

FIG. 6A showed that the COI value of HIV Ag & Ab positive panel decreased in the presence of maltoheptaose and β-cyclodextrin. The competition occurred when 10 mM maltoheptaose or β-cyclodextrin was added to the RoSBD coated plate, strongly indicating that maltoheptaose and β-cyclodextrin could act as competitors for RoSBD binding to HIV Ag & Ab positive panel, and the competitive inhibition rate of 10 mM maltoheptaose and β-cyclodextrin was respectively 24.4% and 23.1%.

Figure 6B:
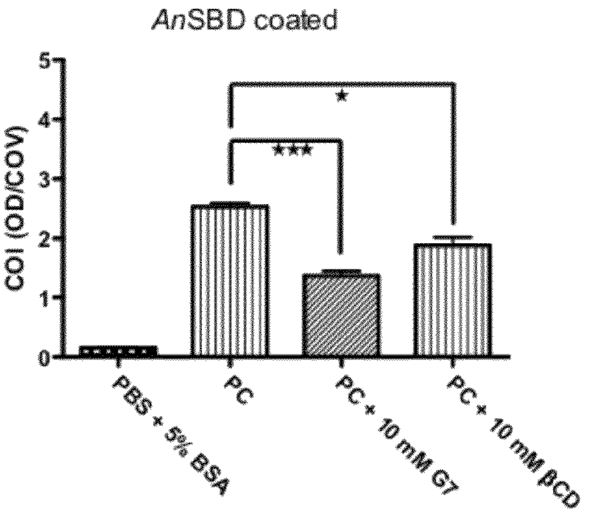

Similarly, the competition occurred when 10 mM maltoheptaose or β-cyclodextrin (βCD) was added to AnSBD (FIG. 6B), suggesting that maltoheptaose or β-cyclodextrin (βCD) could also act as an competitor for AnSBD binding to HIV Ag & Ab positive panel. The competitive inhibition rate of 10 mM maltoheptaose was 45.9%, higher than the competition result of RoSBD. But the competitive inhibition rate of 10 mM β-cyclodextrin was lower (14.3%).

Example 6

Competition Effects of 2G12 and gp140 to HIV-RoSBD and HIV-AnSBD Binding

HIV Ag & Ab positive panel was separately mixed with the same volume of 500 nM human $IgG_1$ secondary antibody, 2G12 monoclonal antibody, and 250 nM HIV1 gp140 antigen at 37° C. for 1 hr. After adding the mixture to (a) RoSBD coated (100 nM in 0.05 M Tris-Hcl, pH 8) and (b) AnSBD coated plate (100 nM in 0.05 M sodium bicarbonate buffer, pH 9.5) individually at 37° C. for 1 hr, 100 μL HRP coupled HIV1 recombinant gp120 antigen conjugate (0.05 μg/mL) was used for detection.

Figure 7A:
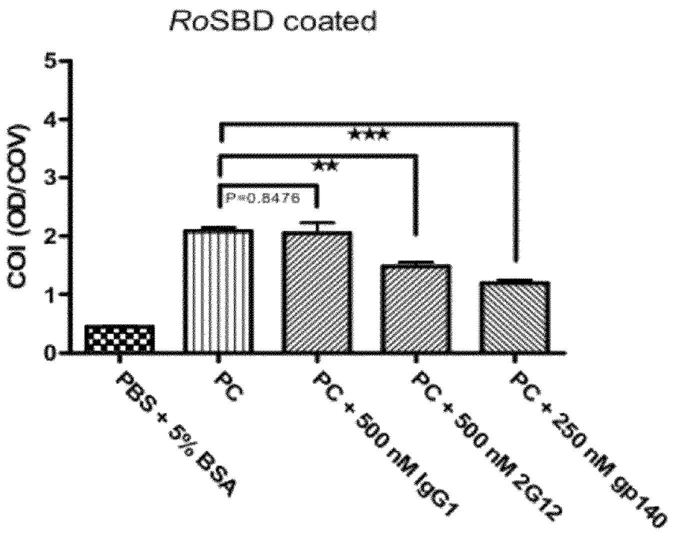
FIGS. 7A and 7B show competition of HIV-RoSBD and HIV-AnSBD binding by HIV1 gp140 antigen and 2G12 monoclonal antibody and HIV1 gp140 antigen.
Figure 7B:
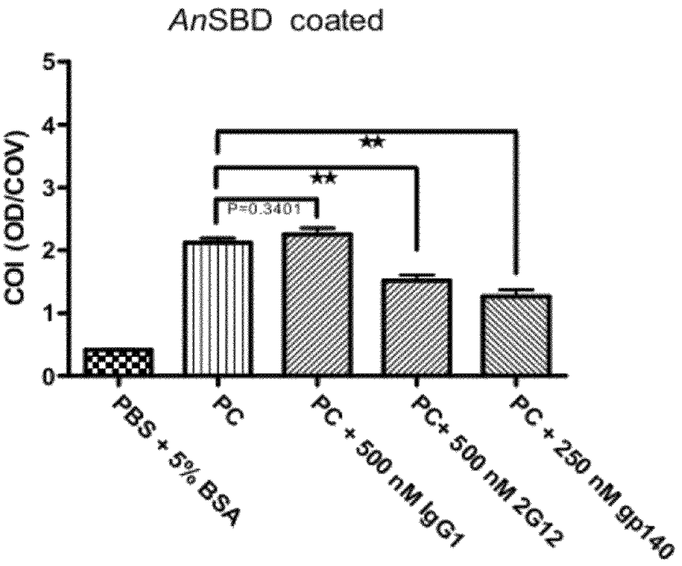

FIGS. 7A and 7B showed that the COI value of HIV Ag & Ab positive panel decreased in the presence of 2G12 human monoclonal antibody. The competition occurred when 500 nM 2G12 was added to the RoSBD (FIG. 6A) and AnSBD (FIG. 6B) coated plate. These results indicated the competition of 2G12 occurred, compared to the negative result of human $IgG_1$. The competitive inhibition rate of 500 nM 2G12 was 28.9% on RoSBD and 28.4% on AnSBD. In contrast, no competition was observed in the presence of 500 nM $IgG_1$. Moreover, the competition was more obvious in the presence of 250 nM HIV1 gp140 with an inhibition rate of 42.9% for RoSBD and 40.1% for AnSBD. These results strongly indicate specific interaction between our SBD and HIV gp120.

Example 7

Amino Acid Sequence Alignment of 2G12 Epitope Region in HIV1 Isolates

FIGS. 8A and 8B illustrates multiple sequence alignment of the 2G12 human monoclonal antibody epitope region of twenty-one HIV1 isolates (SEQ ID NO: 4 to SEQ ID NO: 23) were compared (SEQ ID NO: 3). The 2G12 epitope covers mainly on the high-mannose or hybrid glycans of residue N295, N332, N339, N386, N392, and N448 on gp120 of HIV1 IIIB and JR-FL isolates (Sanders R W, et al., J. Virol. (2002) 76: 7293-7305 and Scanlan C N, et al., J. Virol. (2002) 76: 7306-7321). These Asn residues were evidently highly conserved in all gp120 sequences of 21 HIV1 isolates. The six N-linked glycosylation sites underlined at positions Asn1, Asn38, Asn92, Asn98, Asn103, and Asn154 in FIGS. 7A and 7B corresponded to the 2G12 recognition sites. Moreover, Asn38 and Asn98 were identified as high mannose glycan recognition sites by HIV1 gp120 modeling (Calarese D A, et al., Science (2003) 300: 2065-2071). The results indicate that although HIV exhibits rapid genetic diversification, their N-linked glycosylation sites are stable over time, which makes unique glycans linked these sites good target for specific recognition. The CBM-mediated carbohydrate recognition could thus be used as an antibody mimetic for HIV detection and may further be applied to as a prevention and treatment agent for divergent strains of HIV infection.

What is claimed is:

1. A method of detecting human immunodeficiency virus type 1 (HIV-1) envelope glycoprotein comprising the following:

(a) preparing a solid surface to which is bound a known quantity of carbohydrate binding module (CBM) 20 or 21;

(b) contacting the solid surface with a subject sample;

(c) incubating the sample with the surface under conditions that facilitate CBM binding to any HIV-1 envelope glycoprotein present in the sample thereby forming a CBM-envelope complex;

(d) continuing the incubation under conditions that facilitate binding of the CBM-envelope complex to anti-HIV-1 antibodies that may be present in the sample thereby forming a CBM-envelope-anti-HIV-1 antibody complex;

(e) adding a labeled HIV-1 envelope conjugate to the mixture, wherein the conjugate binds to the anti-HIV-1 antibody present in the CBM-envelope-anti-HIV-1 antibody complex, and (f) measuring the signal intensity from the labeled complex.

2. The method of claim 1, wherein the labeled HIV-1 envelope conjugate is a recombinant HIV-1 envelope conjugated with a signal generating enzyme, which is capable of producing the signal when contacted with a substrate.

3. The method of claim 1, wherein the CBM 20 or CBM 21 is starch binding domain (SBD).

4. The method of claim 1, wherein the CBM 21 is derived from *Rhizopus oryzae* glucoamylase (RoSBD).

5. The method of claim 1, wherein the CBM 20 is derived from *Aspergillus niger* glucoamylase (AnSBD).

6. The method of claim 1, wherein the sample is a plasma, a serum or a blood.

7. The method of claim 1, wherein the subject is a human.

8. The method of claim 2, wherein the signal generating enzyme is horseradish peroxidase (HRP), alkaline phosphatase (AP), peroxidase or beta-galactosidase.

9. The method of claim 2, wherein the substrate is an enzyme substrate for use with the signal generating enzyme.

* * * * *